United States Patent
Eaton

[11] Patent Number: 6,086,801
[45] Date of Patent: Jul. 11, 2000

[54] METHOD FOR FORMING A BREAST PROSTHESIS

[75] Inventor: L. Daniel Eaton, Little Rock, Ark.

[73] Assignee: Board of Trustees of the University of Arkansas, Little Rock, Ark.

[21] Appl. No.: 09/167,080

[22] Filed: Oct. 6, 1998

[51] Int. Cl.[7] .................................................. B29C 39/02
[52] U.S. Cl. ...................... 264/40.1; 264/222; 264/225; 264/227; 264/554; 623/7; 623/8; 623/901
[58] Field of Search .................................. 623/7, 8, 901; 264/40.1, 554, 161, 224, 225, 227, 299, 222

[56] References Cited

U.S. PATENT DOCUMENTS

| | | | |
|---|---|---|---|
| 2,508,156 | 5/1950 | Gillman | 264/225 |
| 2,580,264 | 12/1951 | Wright et al. . | |
| 3,021,569 | 2/1962 | Lyman | 264/225 |
| 3,065,511 | 11/1962 | Leitzel | 264/225 |
| 4,086,666 | 5/1978 | Vaskys et al. . | |
| 4,364,880 | 12/1982 | Howse . | |
| 4,401,492 | 8/1983 | Pfrommer . | |
| 4,600,551 | 7/1986 | Erb . | |
| 4,661,187 | 4/1987 | Beasley . | |
| 4,676,795 | 6/1987 | Grundei . | |
| 4,735,754 | 4/1988 | Buckner . | |
| 5,108,686 | 4/1992 | Griffin | 264/222 |
| 5,169,578 | 12/1992 | Fukao | 264/56 |
| 5,527,359 | 6/1996 | Nakamura et al. . | |

*Primary Examiner*—Jan H. Silbaugh
*Assistant Examiner*—Dae Young Lee
*Attorney, Agent, or Firm*—J. Charles Dougherty

[57] ABSTRACT

A method for forming the outer surface of a breast prosthesis is disclosed. A digital, three-dimensional image is formed of a patient's breast using a computerized scanner. A computer-controlled milling machine utilizes the image to form a solid model of the breast. A sheet of flexible, moldable material having a uniform, precise thickness is then vacuum-formed over the breast model. A hard, two-piece mold is cast from the flexible sheet. A soft, curable material is then either poured or injected between the two pieces of the mold to form the breast prosthesis outer surface. The breast prosthesis outer surface is then turned inside out to form a shape that is a mirror image of the patient's breast.

8 Claims, 4 Drawing Sheets

METHOD FOR FORMING A BREAST PROSTHESIS

BACKGROUND OF THE INVENTION

The present invention relates to a method for forming a breast prosthesis, and in particular to a method for forming a breast prosthesis that has a precisely uniform surface thickness and is shaped to mirror the existing breast when held in a brassiere. To form the mold for the prosthesis, a plastic sheet is formed into the shape of the natural breast. Once molds are made using this plastic sheet, the breast prosthesis outer surface may be formed within the molds. This outer surface is then turned inside out to form the outer surface for a breast prosthesis that is the mirror image of the natural breast.

The purpose of the disclosed invention is to create a comfortable, natural-appearing breast prosthesis for a patient that has lost one of her natural breasts. Typically the natural breast is lost as a result of a mastectomy procedure, although this invention may be utilized regardless of the reason the patient requires the prosthesis. A breast prosthesis should ideally mirror the size, shape, and texture of the remaining natural breast as closely as possible. In this way the patient's goal of appearing to have two natural breasts is most nearly achieved. Since the breast prosthesis is generally only worn while the patient is wearing a brassiere or other support garment, the shape of the breast prosthesis should mirror the shape of the patient's remaining natural breast while that breast is supported.

Other methods for forming a breast prosthesis shaped to mirror an existing natural breast are known in the art. U.S. Pat. No. 2,580,264 to Wright, et al. discloses a method of producing a mold for an artificial breast by turning a mold taken from the existing breast inside out. In the Wright, et al. process, a plaster of Paris mold is taken of the existing breast. A coating of quick-drying liquid latex rubber is then applied inside the plaster of Paris mold. When dried, the latex rubber forms a flexible casing that may be removed from the plaster of Paris mold. The latex rubber casing is turned inside out to form a mold for the artificial breast that will be a mirror image of the existing breast.

U.S. Pat. No. 5,527,359 to Nakamura et al. also discloses a method of producing a mold for an artificial breast by turning a mold taken from the existing breast inside out. In the Nakamura et al. process, a model of the existing breast is formed using aluminum foil. The aluminum model is then filled with plaster to form a positive model of the existing breast. The positive model is then coated with aluminum foil reinforced by thin adhesive taping. The aluminum foil/adhesive taping complex is then turned inside out to form a negative model of the artificial breast.

Other methods are also known for forming a breast prosthesis in the shape of a breast held in place by a support garment. U.S. Pat. No. 4,086,666 to Vaskys et al. discloses a method for forming a breast prosthesis in the shape of a supported breast. In addition to using a cast made of the patient's chest while not wearing a brassiere, a cast is also made of the patient's chest while wearing a brassiere. The negative cast is simply formed over the brassiere itself. A sculptor then uses the positive cast of the supported breast/brassiere combination to help visualize the appearance of the supported breast. Alternatively, Vaskys et al. discloses that measurements may be made of the patient's remaining natural breast while the patient is wearing a brassiere to assist the sculptor in forming a prosthesis in the shape of a supported breast.

U.S. Pat. No. 4,600,551 to Erb discloses a method for producing a breast prosthesis that is symmetrical to the shape of the remaining natural breast while that breast is held in a zero-gravity state. After a molding material is applied to the natural breast, the patient is immersed in a liquid that is of a density essentially equivalent to the density of the natural breast. The mold then cures while the breast is suspended in the liquid. The process thus results in a prosthesis that does not require the artistic interpretation of a sculptor to remove the effects of gravitational stress. However, Erb discloses that the shape of the breast in a zero-gravity state does not strictly conform to the shape of the breast while supported in a brassiere.

Erb also discloses a method of forming a breast prosthesis using a mold formed from a breast supported by a half-brassiere. The half-brassiere is taped to the patient's chest wall and a mold material is formed over the natural breast and brassiere. This approach results in a mold that reflects not the texture of the natural breast only, but also the texture of the brassiere and supporting tape, and thus requires the use of a sculptor in forming the prosthesis.

The prior art methods of forming a breast prosthesis each have a number of disadvantages. First, some of these methods require a human sculptor to form molds for the prosthesis from models. The addition of a sculptor greatly increases the cost and time required for the production of a breast prosthesis. In addition, a human is inherently incapable of exactly reproducing the shape of the existing natural breast in mirror-image form to create a precisely accurate mirror-image prosthesis. Instead, a human must rely on his or her artistic abilities, which inevitably introduces some error into the process.

Another disadvantage of the prior art methods is that the exterior surface of the resulting breast prosthesis will not be of uniform thickness. Simply pouring or painting a curable material onto a smooth surface will result in a cured material that is smooth on only the side that is in contact with the smooth surface. The other side of the cured material will inevitably be wavy, resulting in a cured material of nonuniform thickness. The thickness and consistency of the prosthesis surface is critical for several reasons. First, a material that has thin spots may tend to "balloon" at the thin points, resulting in a misshapen prosthesis. On the other hand, a material that is too thick will result in a prosthesis that does not feel to the touch like a natural breast. Finally, a prosthesis that has an exterior surface of nonuniform thickness will not be as nearly symmetrical with the remaining natural breast as would otherwise be possible using a consistently flat exterior surface material.

Still another disadvantage of the prior art methods for forming a breast prosthesis is the inability to form an accurate image of a breast held in a brassiere or other support garment. This shape is preferred by patients because the prosthesis will typically be worn only while the patient is wearing a support garment. Since a natural breast necessarily sags somewhat due to gravity, a prosthesis formed in the shape of a natural breast will not be symmetrical to the remaining natural breast when a support garment is worn. The Erb method of forming a breast prosthesis while the natural breast is suspended in a controlled-density liquid is awkward, expensive, and would likely cause considerable embarrassment to the patient who must enter this liquid while her upper body is exposed. Moreover, the Erb disclosure indicates that the shape of a breast in this zero-gravity state does not correspond to the shape of a breast held in a supported garment, so the resulting prosthesis would still not mirror the patient's remaining natural breast. The other method disclosed by Erb, that of forming a mold over the patient's remaining natural breast while wearing a half-brassiere, requires additional work by an artist to remove the effects of the brassiere on the mold, which would increase the cost and time required to construct the prosthesis.

SUMMARY OF THE INVENTION

The present invention is a method for forming a breast prosthesis that is a mirror image of the remaining natural breast while overcoming the limitations of prior art methods. The method begins with a computerized scan of the chest of the patient. This scan is performed while the patient's natural breast is supported. This computerized scan results in a three-dimensional image file stored on a computer storage medium. The image file may be transmitted to a remote facility for the production of the prosthetic breast.

At the production facility, the image of the remaining natural breast is employed by a computer-controlled milling machine to form an image of the natural breast. The material from which the breast shape is milled may be either a hard resin or a softer material. If a soft material is used, it is typically necessary to take an impression of the milled breast shape which is then cast in a hard resin to form a positive image of the remaining natural breast.

The positive cast is then placed in a vacuum molding machine where a thin sheet of plastic is heated and vacuum formed to the shape of the cast. The plastic sheet is of a precisely measured and consistent thickness. After the vacuum-forming operation is complete, the thin plastic sheet is then in the form of the patient's natural breast.

The plastic sheet is then used to form a two-piece plaster mold. One piece of this mold will be a positive model of the patient's natural breast; the positive model will fit into the other piece forming a negative model of the patient's breast. A curable material such as Silastic is then injected between the two pieces of the mold to form the outer surface of the breast prosthesis. The Silastic outer surface is then turned inside out to form the prosthesis outer surface, which will thus have a shape that is the mirror image of the patient's breast. The resulting breast prosthesis exterior will be of uniform thickness and will feel to the touch quite similar to a natural breast.

This process results in a number of advantages over the prior art methods. First, no human sculptor is needed at any stage of the disclosed method. This removes inaccuracies due to the sculptor's artistic interpretation, and results in a prosthesis that is a precise mirror image of the patient's natural breast. Moreover, the cost and delay involved with the use of a sculptor are eliminated.

Another advantage is that the disclosed method allows the production of a breast prosthesis having a surface with a precisely controlled thickness and uniformity. This eliminates problems with ballooning, and allows the production of a prosthesis that feels to the touch as much like a natural breast as possible.

Also, the disclosed method allows the production of a prosthesis that mirrors the precise shape of the patient's natural breast while held in a support garment. Thus the prosthesis will appear as natural as possible during the patient's daily activities.

It is therefore an object of the present invention to provide for a breast prosthesis that is the precise mirror image of an existing natural breast.

It is a further object of the present invention to provide for a breast prosthesis that has an exterior surface of a precise and consistent thickness.

It is also an object of the present invention to provide a breast prosthesis that is in the shape of a natural breast supported by a brassiere or other support garment.

These and other objects and advantages of the present invention will be apparent from a consideration of the following detailed description of the preferred embodiments in conjunction with the appended drawings as described following.

DETAILED DESCRIPTION OF THE PREFERRED EMBODIMENTS

With reference to FIGS. 1–5, a preferred embodiment of the disclosed invention may be described. The disclosed method begins with the formation of a three-dimensional image of the patient's breast. This image is created using a scanning device (not shown) as is well known in the art and has been applied to a myriad of modeling applications. Preferably, the scanning device includes a camera mounted on a support that allows the camera to rotate 180° around the object of interest. The result of this scanning process is a series of two-dimensional images of the object of interest from various angles as the camera moves around the object. Computer software resolves these multiple two-dimensional images into a three-dimensional image of the object.

To form a three-dimensional image of the patient's breast, the patient is positioned so that the scanning device's camera will move in an arc around the patient's breast. The patient is fitted with a support garment during the scanning operation so that the resulting prosthesis will mirror the patient's natural breast while similarly supported; preferably this support garment would be a brassiere that is cut away so that only half of the cup remains beneath the patient's breast. A three-dimensional image of the patient's supported breast is then formed from the images taken as the camera moves around the patient's breast. Because the support garment only covers the lower portion of the patient's breast, the resulting image will only be minimally affected by the presence of the support garment. Any irregularities in the image of the patient's breast as a result of the support garment may be smoothed away using appropriate image-processing software, as is well known in the art.

The three-dimensional image file is stored on a computer storage medium, such as magnetic disks or a CD-ROM. Since the image file is stored in a digital format, it may be quickly and easily transferred to a remote production facility either by modem or by the shipment of a computer diskette, CD-ROM, or other electronic storage medium containing the image file. In addition, this image may be maintained on file so that should the patient need an additional or replacement prosthesis mold produced, the patient will not be required to undergo the scanning process again.

Figure 1:
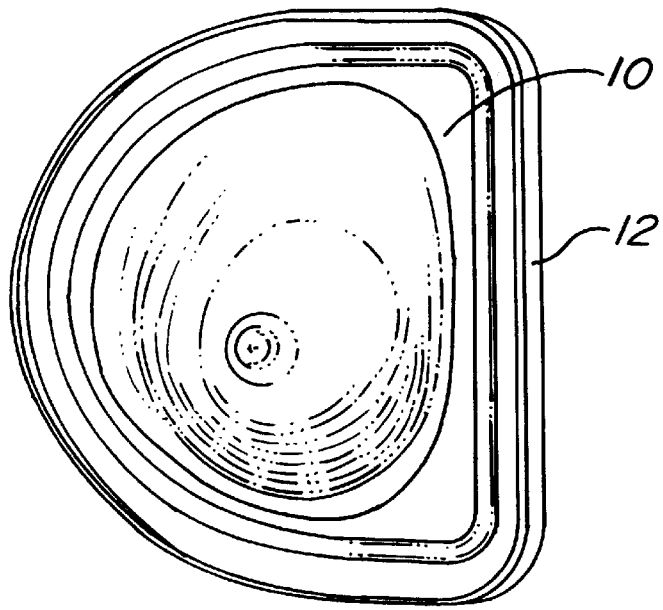
FIG. 1 is a perspective view of a positive model of a patient's natural breast produced from a computer-controlled milling machine using a three-dimensional computerized image.

At the production facility, the image of the natural breast is employed by a computer-controlled milling machine to cut a three-dimensional form in the shape of the natural breast. The material from which the breast-shaped form is milled is preferably a hard resin. If a soft material is used, it is necessary to take an impression of the milled breast-shaped form which is then cast in harder material to form a positive image of the breast. In either case, the result of this process is breast positive mold 10, as shown in FIG. 1. Mold base 12 is preferably formed as an integral support for breast positive mold 10.

Figure 2:
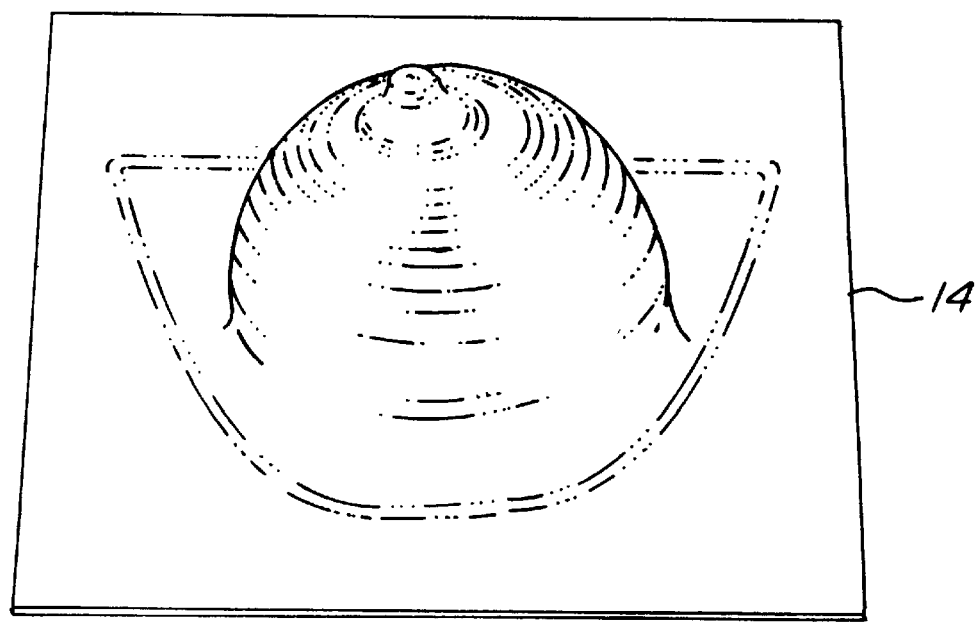
FIG. 2 is a perspective view of a thin plastic sheet that was vacuum-formed over the positive model of the patient's natural breast.

Referring now to FIG. 2, plastic sheet 14 is shown. While plastic sheet 14 is preferably made of vinyl, any other material, whether plastic or otherwise, may be used, provided such material is sufficiently pliable and moldable to form the necessary shape of the breast prosthesis. Plastic sheet 14 should be of uniform thickness since the thickness of plastic sheet 14 will be reflected in the thickness of prosthesis surface 20 (shown in FIGS. 5 and 6) as described hereafter. If plastic sheet 14 has thin areas, the resulting prosthesis surface 20 will tend to "balloon" at these thinner points, resulting in a misshapen prosthesis or a rupture of the prosthesis surface 20 due to wear. On the other hand, prosthesis surface 20 must be thin since otherwise it will not feel to the touch like a natural breast. Experiments have shown that a plastic sheet 14 having a consistent thickness of about 1.9 mm produces a prosthesis surface 20 that is appropriately thin to simulate the feel of a natural breast but is still able to withstand everyday wear without damage.

To form plastic sheet 14 into the shape shown in FIG. 2, plastic sheet 14 is placed over breast positive mold 10 in a vacuum-forming machine of conventional design (not shown). Plastic sheet 14 is then heated and vacuum formed such that it forms into the shape of breast positive mold 10 as shown in FIG. 2. After the vacuum-forming operation is complete, plastic sheet 14 then forms an exact image of the patient's natural breast.

Figure 3:
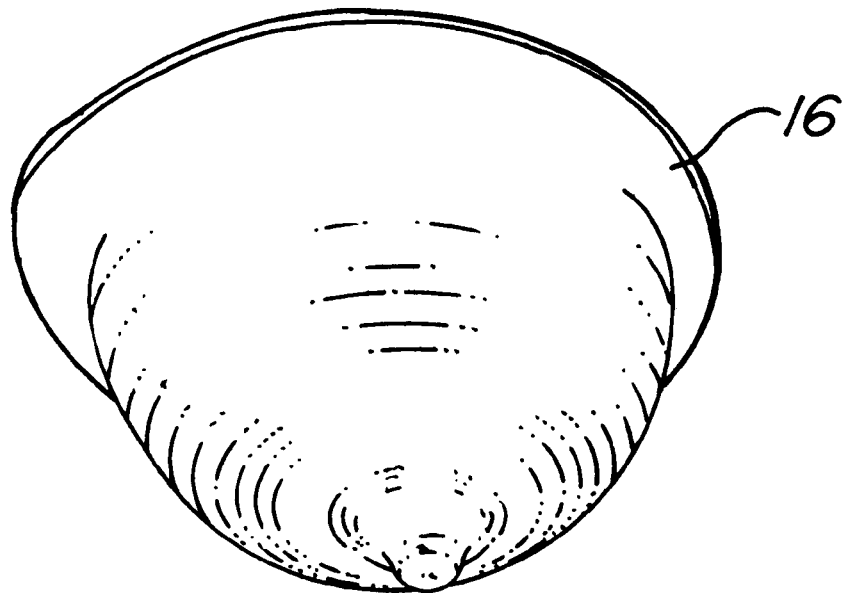
FIG. 3 is an exploded view of the two-piece mold formed from the plastic sheet.
Figure 3:
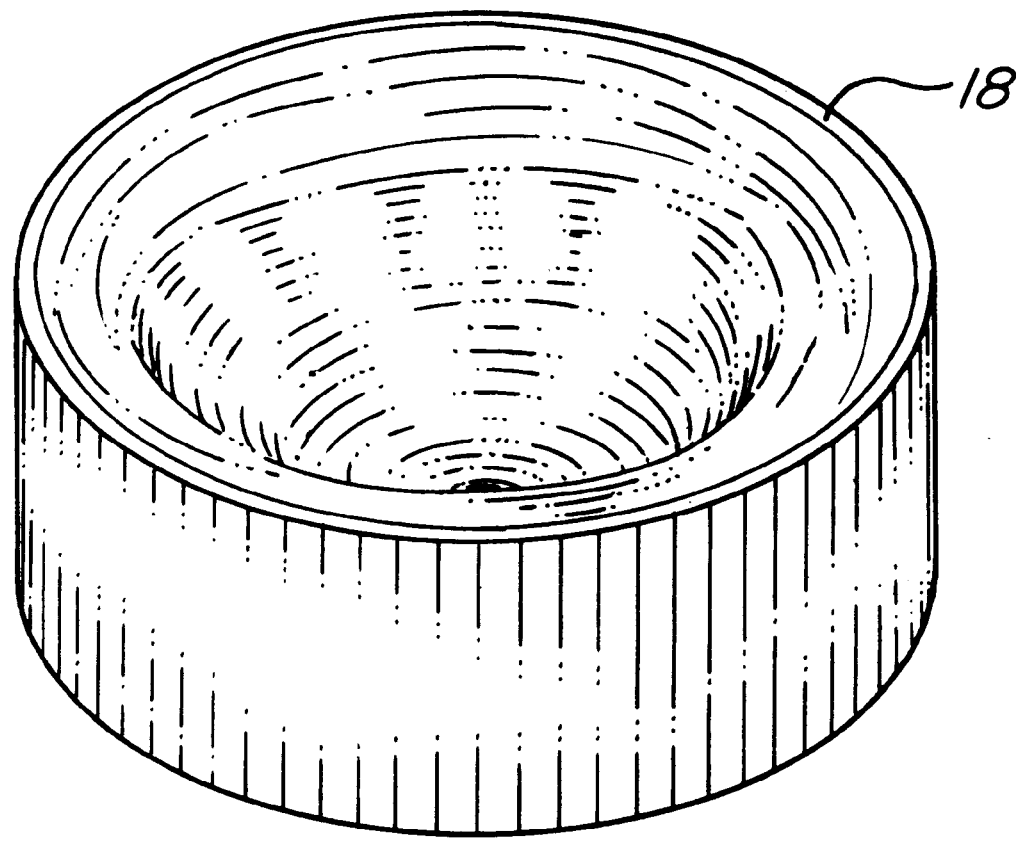

Plastic sheet 14 is next used to form a two-piece plaster mold, consisting of positive prosthesis mold 16 and negative prosthesis mold 18, as shown in FIG. 3. Positive prosthesis mold 16 is formed by pouring a hard-curing plaster material into the cup formed by plastic sheet 14 and allowing the material to cure. Positive prosthesis mold 16 thus forms a model of the patient's natural breast. Negative prosthesis mold 18 is formed by pouring the hard-curing plaster material into a cylindrical container (not shown) and then pressing plastic sheet 14 into the plaster material while prosthesis mold 16 is still within plastic sheet 14. Once negative prosthesis mold 18 dries, it will form a negative model of the patient's natural breast, although it will of course be slightly larger than the patient's natural breast due to the thickness of plastic sheet 14.

Figure 4:
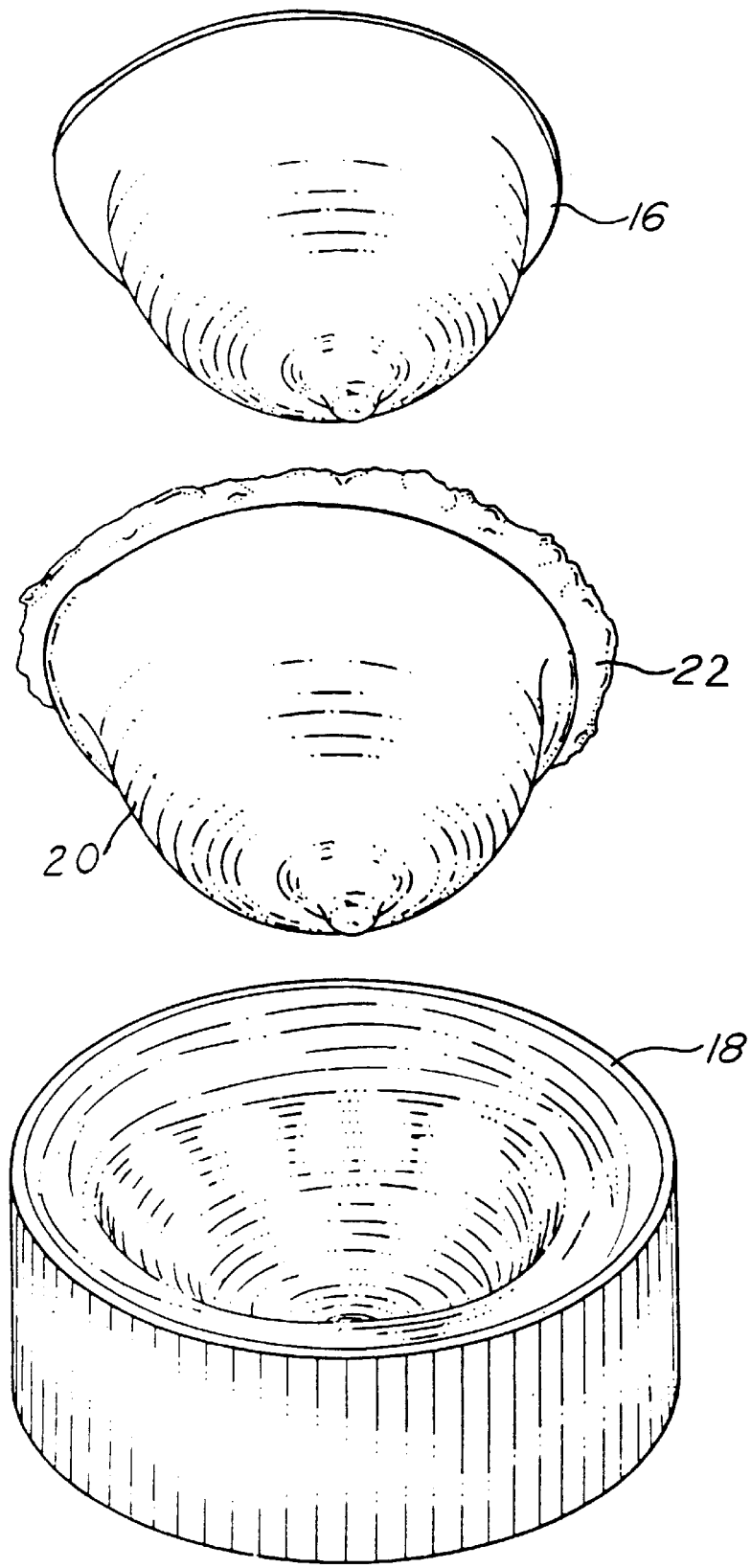
FIG. 4 is an exploded view of the two-piece mold, as well as the Silastic exterior of the breast prosthesis formed within the two-piece mold.

A soft, curable material is then used to form prosthesis surface 20 as shown in FIG. 4. SILASTIC, a room temperature, vulcanizable silicone product that is widely available and is manufactured by Dow Corning, has been found to be effective for forming prosthesis surface 20. In one method of forming prosthesis surface 20, SILASTIC is poured into negative prosthesis mold 18, and then positive prosthesis mold 16 is placed within negative prosthesis mold 18. Alternatively, Silastic could be injected between positive prosthesis mold 16 and negative prosthesis mold 18. The resulting breast prosthesis surface 20 will be of uniform thickness, mimicking the thickness and shape of plastic sheet 14.

Figure 5:
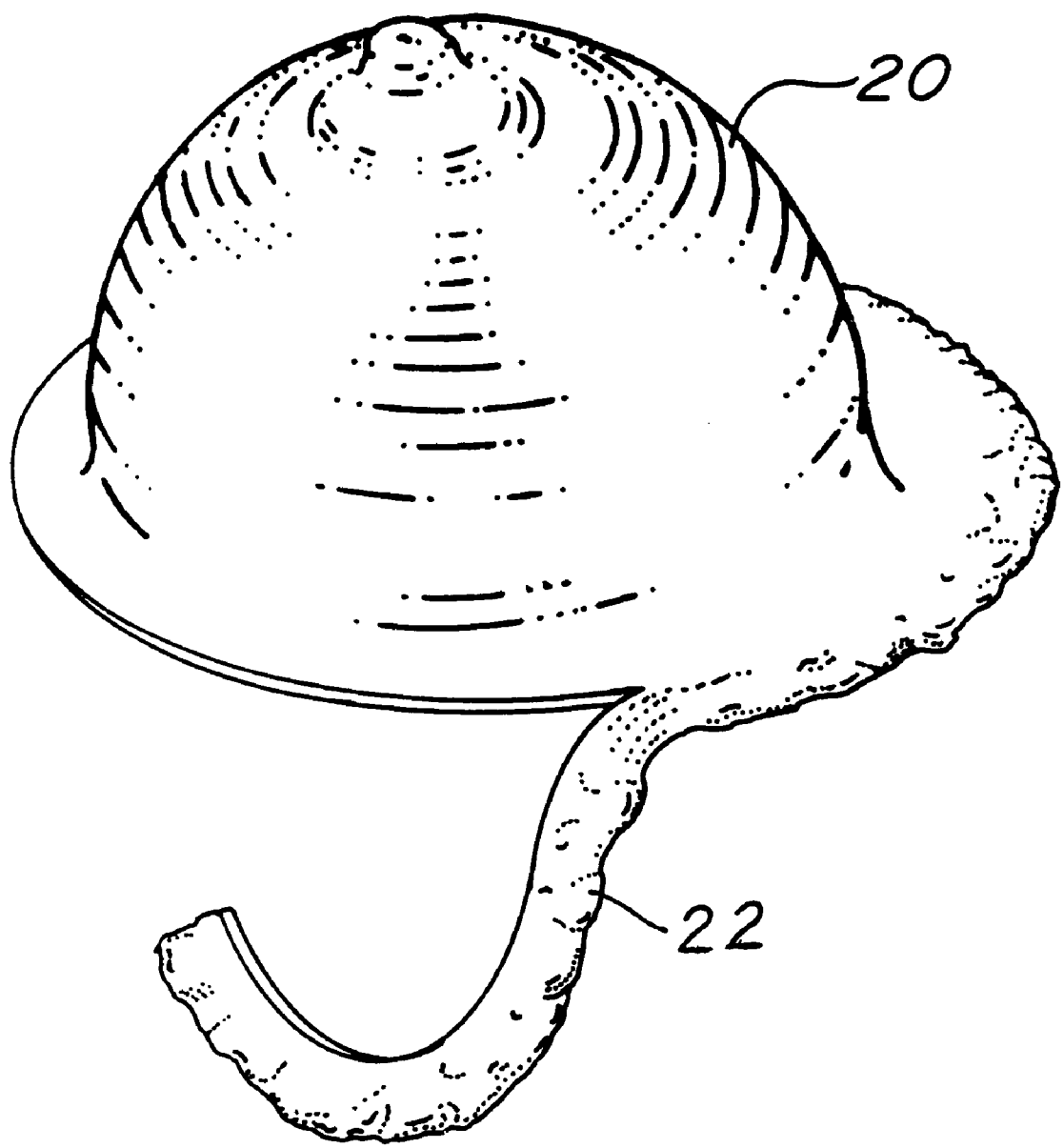
FIG. 5 is a perspective view of the SILASTIC exterior of the breast prosthesis after it has been turned inside out.

Once prosthesis surface 20 is dry, it may be removed from the mold and turned inside out as shown in FIG. 5. Once prosthesis surface 20 is turned inside out, it forms a shape that is the precise mirror image of the patient's natural breast. Prosthesis surface 20 can then be trimmed for a smooth edge by removing flashing 22. To form the complete prosthesis, the prosthesis surface 20 may be filled with a gel material, and a rear portion (not shown) can be attached in a conventional manner to finish the prosthesis.

In an alternative embodiment of the invention, plastic sheet 14 may be turned inside out before positive prosthesis mold 16 and negative prosthesis mold 18 are formed. In this embodiment, positive prosthesis mold 16 would be a model of the mirror image of the patient's natural breast rather than a model of the breast itself. It would be unnecessary to turn prosthesis surface 20 inside out after it is formed since it would already be in the shape of the mirror image of the patient's natural breast.

The present invention has been described with reference to certain preferred and alternative embodiments which are intended to be exemplary only and not limiting to the full scope of the present invention as set forth in the appended claims.

What is claimed is:

1. A method for forming a breast prosthesis comprising the method steps of:

(a) producing a three-dimensional image of a breast by performing a computerized scan of the breast;

(b) producing a positive model of the breast based on said three-dimensional image;

(c) vacuum-forming a uniformly flat flexible sheet having a consistent thickness over said positive model such that said flexible sheet is molded into the shape of said positive model thereby forming an interior side and exterior side;

(d) casting a two-piece solid mold from said flexible sheet, said two piece mold comprising a first piece formed over the exterior side of said flexible sheet, and said second piece formed within the interior side of said flexible sheet;

(e) introducing a curable material into said mold between said first piece and said second piece to form a breast prosthesis having an inner surface and an outer surface and having a consistent thickness; and (f) turning said breast prosthesis inside out such that said inner surface becomes the outer surface of said breast prosthesis to form a precise mirror image of the breast.

2. The method of claim 1, wherein said thickness of said flexible sheet is about 1.9 millimeters.

3. The method of claims 2, wherein said flexible sheet comprises vinyl.

4. The method of claim 1, wherein the breast is held in a support garment during step (a).

5. The method of claim 4, wherein said support garment comprises a half-cup fitted underneath the breast.

6. The method of claim 1, wherein said curable material is silicone material.

7. The method of claim 1, wherein step (a) is performed using a camera on a 180° mount.

8. The method of claim 1, wherein step (b) is performed using a computer-controlled milling machine.

* * * * *